United States Patent
Sorenson et al.

(10) Patent No.: US 9,617,504 B2
(45) Date of Patent: Apr. 11, 2017

(54) NON-MEDICATED PERSONAL CARE CLEANSING SOLUTION AND A METHOD OF SYNTHESIZING THE SAME

(71) Applicants: Scott Robert Sorenson, Oakland Park, FL (US); Scott Paul Sorenson, Oakland Park, FL (US)

(72) Inventors: Scott Robert Sorenson, Oakland Park, FL (US); Scott Paul Sorenson, Oakland Park, FL (US)

( * ) Notice: Subject to any disclaimer, the term of this patent is extended or adjusted under 35 U.S.C. 154(b) by 44 days.

(21) Appl. No.: 14/861,265

(22) Filed: Sep. 22, 2015

(65) Prior Publication Data

US 2016/0010039 A1    Jan. 14, 2016

(51) Int. Cl.

| | |
|---|---|
| *C11D 9/02* | (2006.01) |
| *C11D 9/38* | (2006.01) |
| *C11D 9/22* | (2006.01) |
| *C11D 9/26* | (2006.01) |
| *C11D 9/36* | (2006.01) |
| *C11D 13/00* | (2006.01) |
| *A61K 8/58* | (2006.01) |
| *A61Q 19/10* | (2006.01) |
| *A61K 8/891* | (2006.01) |
| *A61K 8/894* | (2006.01) |
| *C11D 3/20* | (2006.01) |
| *C11D 3/37* | (2006.01) |
| *C11D 3/382* | (2006.01) |

(Continued)

(52) U.S. Cl.
CPC ............... *C11D 9/02* (2013.01); *A61K 8/585* (2013.01); *A61K 8/891* (2013.01); *A61K 8/894* (2013.01); *A61Q 19/10* (2013.01); *C11D 3/2068* (2013.01); *C11D 3/2093* (2013.01); *C11D 3/373* (2013.01); *C11D 3/382* (2013.01); *C11D 3/50* (2013.01); *C11D 9/225* (2013.01); *C11D 9/26* (2013.01); *C11D 9/267* (2013.01); *C11D 9/36* (2013.01); *C11D 9/38* (2013.01); *C11D 10/045* (2013.01); *C11D 11/0094* (2013.01); *C11D 13/00* (2013.01); *C11D 17/08* (2013.01); *A61K 2800/31* (2013.01); *C11D 1/82* (2013.01)

(58) Field of Classification Search
None
See application file for complete search history.

(56) References Cited

U.S. PATENT DOCUMENTS

2015/0118165 A1\* 4/2015 Rudolph ............... A01N 31/06
                                                                    424/49
2015/0196570 A1\* 7/2015 Tamarkin ............. A61K 9/0014
                                                                    514/152

\* cited by examiner

*Primary Examiner* — Necholus Ogden, Jr.
(74) *Attorney, Agent, or Firm* — Barry Choobin; Patent 360

(57) ABSTRACT

The embodiments herein disclose a composition for a non-medicated liquid cleaning solution for personal care and hygiene and a method of synthesizing the same. The composition comprises cyclomethicone, DC5225C®, ethyl lactate, sesame oil, Vitamin E, organic castile soap, sweet orange oil or fragrances. For synthesizing the composition, the ingredients are procured. The castile soap is treated to remove water content. All the ingredients except cyclomethicone are mixed to obtain clear solution mixture. The clear solution mixture is added to cyclomethicone. The clear solution mixture and cyclomethicone are mixed to obtain a homogeneous mixture. The composition is sprayed or applied on tissue paper/toilet paper. The composition makes the tissue paper into a moist wipe used for cleaning the body parts like private body parts, groin, face, genital area, groin and rear end.

19 Claims, 2 Drawing Sheets

(51) Int. Cl.
*C11D 3/50* (2006.01)
*C11D 10/04* (2006.01)
*C11D 11/00* (2006.01)
*C11D 17/08* (2006.01)
*C11D 1/82* (2006.01)

NON-MEDICATED PERSONAL CARE CLEANSING SOLUTION AND A METHOD OF SYNTHESIZING THE SAME

BACKGROUND

Technical Field

The embodiments herein generally relates to personal care products. The embodiments herein particularly relate to a non-medicated liquid cleansing solution. The embodiments herein more particularly relate to a water-free, non-medicated liquid cleansing solution used for cleaning a butt or genital regions after using the bathroom or to freshen up.

Description of the Related Art

The personal care products or toiletries include products for personal hygiene. The subsectors of personal care products include personal hygiene and cosmetics. There are distinction between the personal care products and cosmetics. The personal care products include lip balm, cleansing pads, cologne, cotton swabs, cotton pads, deodorants, facial tissue paper, hair clippers, lotion, nail files, pomade, perfume, razors, shaving cream, skin cream, talcum powder, toilet paper, tooth paste, wet wipes, cleansing solution and bathing solution.

The commercial personal care products, specifically body care products within the larger category of personal hygiene products are now widely accepted and used by general public. The research and development of new body care products has been more active from the past decade. The intensity of the competition is driven by the size, world wide scope and growth of the market for personal care category. The global market reportedly generates total revenues more than USD 11 billion annually with a compound annual growth of 37%. The development of new and innovative products is well recognized as essential to continuing competitiveness of companies within this market.

The most common article used in the personal care products are towelettes, often also referred to as wipes. Depending on the intended personal care function or use, the towelette is variously coated or impregnated with different components. The towelettes are categorized as dry or wet wipes. The towelettes are used to deliver disinfectants, surfactants, moisturizers, organic molecules (including vitamins and enzymes), deodorants, and anti-microbial agents to face, body and genitals. Substantial effort is made to develop compositions that are dry to the touch, ready to use (wet), easily applied, resistant to reverse contaminants, perform multiple personal care related functions, convenient in design and use, specifically effective and cost efficient. When multiple personal care related functions are to be performed, the respective compounds must be mutually compatible and functionally non-diluting or separated by an impermeable barrier and applied serially. Beyond the complexity of the constituent components, these compositions must also be stable over practical time and temperature ranges.

Among the personal care products, mainly skin care products or skin conditioning products are used to improve the skin properties such as retention of moisture, softening of the skin, attraction of air moisture, retardation of water loss, reduction of skin irritations caused by contact with cosmetic ingredients, fecal matter or body fluids etc.

Generally two broad areas of skin care products have been recognized as skin conditioners, i.e. emollients and humectants. The emollients generally provide improved moisture retention in the skin and plasticization/softening of the skin. The common commercial emollients are mineral oil, petroleum aliphatic alcohols, such as stearyl alcohol, lanolin and its derivatives, glycerol stearate, and fatty acids (such as trimethanolamine oleate). The humectants generally attract moisture, retard evaporation of water from skin surface and plasticizes/softens the skin. The common commercial humectants include glycerin, propylene glycol, sorbitols and polyethylene glycols.

A desirable personal care composition has to impart at least some of the attributes of an emollient or humectants, as well as to provide an improved lubricity, freshness to skin and reduce skin irritation.

The earlier products and prior arts disclose a dry wipe system based on use of a water soluble matrix holding a non-aqueous liquid composition applied to or permeating a towelette formed by the matrix or a water stable material. The liquid composition is highly soluble in water. The liquid composition is a non-degradable solvent of a solute having germicidal and fungicidal properties. The towelette must be contained in a closed moisture impervious package. Otherwise, the matrix begins to dissolve and release the liquid composition contravening the description as a dry wipe.

Few other products comprise a wet wipe towelette permeated with a multiple component aqueous solution and sealed in a foil packet. The solution included sodium bicarbonate as a neutralizing buffer for a deodorant. It has been reported that sodium bicarbonate has side effects on the skin of the user. Further a long term use of sodium carbonate leads to a dry skin.

Few other prior arts disclose the structural systems for maintaining separate incompatible or undesirably mixed compositions. In the former, a multilayer towelette is sectioned to separate the two portions of the towelette that in turn are impregnated with different non-migratory liquid compositions. A peel-off plastic film is added to further compartmentalize the two separate portions of the towelette, thereby allowing a folding of the towelette. In the latter, the towelette is impregnated with a single non-migratory liquid composition applied so as to leave a dry boarder. The multiple component based compounds are described as alternates for the non migratory liquid composition. In a composition, a complex silicone oil, synthetic esters or hydrocarbon based chemistry is apparently required to achieve a cosmetically acceptable non-migratory carrier that is further compatible with and includes dissolved surfactant organic sun screen agents, anti-microbial or astringents.

Previously, many polysaccharide based materials are available for use in the formulations to treat skin. These materials are mainly solid powder materials. There are three reasons for supplying these materials in a dry powder form as a powder is fairly easy to manufacture, for example, the powder is simply formed from the raw materials without the need to formulate a liquid. Further the dry powder has very little storage problems whereas a liquid starch materials is a possible growth medium for microorganism. Still further, the dry powder does not have the high shipping costs associated with transporting the large volume of water (90-95%) needed to provide a pourable dilute liquid starch solution.

The dry powder form of these polysaccharide based materials, causes difficulties for end use formulators as great care is required to dissolve the dry materials during the formulation process. Water soluble synthetic polymers are used. However the synthesis and formulation of the synthetic polymers makes the product expensive.

The personal care solutions or liquid compositions are used as moisturizers to treat or prevent dry rough, scaly, itchy skin and minor skin irritations (such as diaper rash, skin burns etc). The emollients are substances that soften and moisturize the skin to decrease itching and flaking Some products (such as zinc oxide, white petroleum jelly) are used mostly to protect the skin against irritation (from wetness). Dry skin is caused by a loss of water in the upper layer of the skin. The emollients/moisturizers work by forming an oily layer on the top of the skin that traps water in the skin. Petroleum, lanolin, mineral oil and dimethicone are common emollients. The humectants, including glycerin, lecithin and propylene glycol draw water into the outer layer of skin. Many products also have ingredients that soften the horny substance (keratin) that holds the top layer of skin cells together. The ingredients include but not limited to urea, alpha hydroxyl acids such as lactic/citric/glycolic acid and allatonin. This helps the dead skin cells to face off thereby helping the skin to keep in more water skin cells, and to keep more water to maintain the smoothness and softness of the skin.

Some body care/personal care products cannot be used in sensitive areas such as vaginal/groin area. It has reported that some personal care compositions/solutions exhibit side effects such as burning sensation, stinging, redness or irritation when applied in the vaginal/groin area/genital areas. In some cases allergic reactions including rash itching/swelling are observed/reported in the groin/vaginal/genital areas.

In the prior arts, it has been reported that the water based formulation comprises mainly of witch hazel. The water based formula causes a toilet paper to become brittle and fall apart.

Hence, there is a need for a water-free, non-medicated liquid cleansing solution composition which does not have side effects. Also there is a need for a non-medicated liquid cleansing solution composition which is sprayed on a tissue paper and is easily applied on the specific body area. Further there is a need for a simple method to synthesize the non-medicated liquid cleansing solution composition.

The above mentioned shortcomings, disadvantages and problems are addressed herein and which will be understood by reading and studying the following specification.

OBJECTIVES OF THE EMBODIMENTS

The primary objective of the embodiment herein is to provide a water-free, non-medicated liquid cleansing solution composition.

Another object of the embodiment herein is to provide a non-medicated liquid cleansing solution composition which is sprayed on tissue paper and is easily applied on the specific body area.

Yet another object of the embodiment herein is to provide a non-medicated liquid cleansing solution composition which doesn't contain any harsh/harmful ingredients that cause an allergic reaction.

Yet another object of the embodiment herein is to provide a non-medicated liquid cleansing solution which provides smoothness, soothing and freshness to the skin on the area of application.

Yet another object of the embodiment herein is to provide a non-medicated liquid cleansing solution which when sprayed on tissue paper exhibit similar qualities of a baby wipe.

Yet another object of the embodiment herein is to provide a non-medicated liquid cleansing solution comprising organic castile soap which kills germs and bacteria.

Yet another object of the embodiment herein is to provide a non-medicated liquid cleansing solution which is water free.

Yet another object of the embodiment herein is to provide a non-medicated liquid cleansing solution which is water free and does not get absorbed by toilet paper/tissue paper.

Yet another object of the embodiment herein is to synthesize a non-medicated liquid cleansing solution by an easy method.

These objects and the other advantages of the embodiments herein will become readily apparent from the following detailed description taken in conjunction with the accompanying drawings.

SUMMARY

The various embodiments herein provide a non-medicated liquid cleansing solution composition for personal hygiene and cleansing of private parts. The embodiments herein also provide a water-free, non-medicated liquid cleansing solution composition which is sprayed on tissue paper and is easily applied on the specific body area. Also the non-medicated liquid cleansing solution composition has no side effects. The non-medicated hygienic sanitary spray is used to moisten toilet paper/tissue paper. The non-medicated hygienic sanitary spray turns the toilet paper/tissue paper into a moist wipe. The moist wipe is used to clean the private body parts or any other body part.

According to one embodiment herein, a method of synthesizing a water-free, non-medicated liquid cleaning solution composition for personal care is provided. The method comprises the following steps. The cylomethicone, DC5225C®, ethyl lactate, sesame oil, Vitamin E, organic castile soap, sweet orange oil or a plurality of fragrances are purchased or procured. The organic castile soap is treated to extract the water content. The sesame oil, Vitamin E, ethyl lactate, DC5225C®, sweet orange oil or the plurality of fragrances and the treated organic castile soap are mixed to obtain a clear solution mixture. The clear solution mixture is added to the cyclomethicone. The clear solution mixture and cyclomethicone are mixed to attain a homogeneous mixture. The non-medicated liquid cleansing solution composition is synthesized for personal care and hygiene. The DC5225C® is a silicone surfactant.

According to one embodiment herein, the method of treating organic castile soap to remove water content involves drying the organic castile soap. The method of treating organic castile soap to remove water content comprises the following steps. The liquid organic castile soap is placed in a container. The container comprising liquid organic castile soap is heated. The water content from the organic castile soap is evaporated by applying a constant heat. The organic castile soap is obtained in a solid state.

According to one embodiment herein, the sesame oil is present in a preset quantity of 2.25% v/v. The Vitamin E is present in a preset quantity of 0.51% v/v. The ethyl lactate is present in a preset quantity of 3.24% v/v. The DC5225C® is present in a preset quantity of 3.50% v/v. The sweet orange oil or plurality of fragrances are present in a present quantity of 1.00% v/v. The dried organic castile soap is present in a preset quantity of 0.29% v/v. The cyclomethicone is preset in a preset quantity of 89.21% v/v.

According to one embodiment herein, the non-medicated liquid cleansing solution composition is sprayed or applied on tissue paper/toilet paper. The non-medicated liquid cleaning solution composition makes the tissue paper/toilet paper into a moist wipe. The moist wipe is used for cleaning a plurality of body parts. The moist wipe is specifically used for cleaning private body parts, groin, face, genital area and rear end.

According to one embodiment herein, the cyclomethicone is a volatile carrier. The cyclomethicone is compatible with the DC5225C®, silicone surfactant, ethyl lactate, sesame oil, Vitamin E, organic castile soap, sweet orange oil or the plurality of fragrances. The cyclomethicone is spread on the area of the application.

According to one embodiment herein, the DC5225C® is a delivery system for the non-medicated cleaning solution composition for personal care.

According to one embodiment herein, ethyl lactate is a solvent. The ethyl lactate is water rinsable grease or fat removal agent in the non-medicated liquid cleansing solution composition.

According to one embodiment herein, the sesame oil is a moisturizer in the non-medicated liquid cleansing solution composition. The sesame oil removes toxins from the surface of skin. The sesame oil is an anti-oxidant agent, and wherein the sesame oil is an anti-bacterial agent.

According to one embodiment herein, the organic castile soap kills bacteria and germs.

According to one embodiment herein, the sweet orange oil or plurality of fragrances are added in non-medicated liquid cleansing solution composition for personal care to eliminate bad odour from the body parts.

According to one embodiment herein, a water-free, non-medicated liquid cleaning solution composition for personal care, is provided. The composition comprises cyclomethicone, DC5225C®, ethyl lactate, sesame oil, Vitamin E, organic castile soap and sweet orange oil or plurality of fragrances. The DC5225C® is a silicon surfactant.

According to one embodiment herein, the sesame oil is present in a preset quantity of 2.25% v/v. The Vitamin E is present in a preset quantity of 0.51% v/v. The ethyl lactate is present in a preset quantity of 3.24% v/v. The DC5225C® is present in a preset quantity of 3.50% v/v. The sweet orange oil or plurality of fragrances are present in a present quantity of 1.00% v/v. The dried organic castile soap is present in a preset quantity of 0.29% v/v. The cyclomethicone is preset in a preset quantity of 89.21% v/v.

According to one embodiment herein, the cyclomethicone is a volatile carrier. The cyclomethicone is compatible with the DC5225C®, silicone surfactant, ethyl lactate, sesame oil, Vitamin E, organic castile soap, sweet orange oil or plurality of fragrances. The cyclomethicone is spread on the area of the application.

According to one embodiment herein, the DC5225DC® is a delivery system for the non-medicated cleaning solution composition for personal care.

According to one embodiment herein, the ethyl lactate is a solvent. The ethyl lactate is water rinsable grease or fat removal agent in the non-medicated liquid cleansing solution composition.

According to one embodiment herein, the sesame oil is a moisturizer in the non-medicated liquid cleansing solution composition. The sesame oil removes toxins from the surface of skin. The sesame oil is an anti-oxidant agent and the sesame oil is an anti-bacterial agent.

According to one embodiment herein, the organic castile soap kills bacteria and germs.

According to one embodiment herein, the sweet orange oil or plurality of fragrances are added in non-medicated liquid cleansing solution composition for personal care to eliminate bad odour from the body parts.

According to one embodiment herein, the non-medicated liquid cleansing solution composition is sprayed or applied on tissue paper/toilet paper. The non-medicated liquid cleansing solution composition makes the tissue paper/toilet paper into a moist wipe. The moist wipe is used for cleaning plurality of body parts. The moist wipe is specifically used for cleaning private body parts, groin, face, genital area and rear end.

According to one embodiment herein, the non-medicated liquid cleansing solution composition is intended to be sprayed on toilet paper/tissue paper. The non-medicated liquid cleansing solution composition is sprayed on toilet paper/tissue paper and applied on the specific body area (such as groin, or private body parts) to give a smoothness and soothing feeling. The non-medicated liquid cleansing solution composition when sprayed on toilet paper/tissue paper gives qualities that are similar to that of a baby wipe. The non-medicated liquid cleansing solution composition does not contain any harsh/harmful ingredients that cause an allergic reaction in people.

According to one embodiment herein, the non-medicated liquid cleansing solution composition comprises cyclomethicone, DC5225C® silicone surfactant, ethyl lactate, sesame oil, vitamin E, Castile soap, sweet orange oil and plurality of fragrances.

According to one embodiment herein, cyclomethicone is added in a quantity of 89.21% v/v for the synthesis of non-medicated liquid cleansing solution composition. The cyclomethicone is a volatile carrier, compatible with a wide range of cosmetic ingredients. The cyclomethicone has a low surface tension. The advantage of cyclomethicone in the composition is that the composition imparts soft and silky skin after application. Further, the composition is spread uniformly on the area of application and has a non-greasy nature.

According to one embodiment herein, DC5225C® is a silicone surfactant. The DC5225C® is added in a quantity of 3.50% v/v for the synthesis of non-medicated liquid cleansing solution composition. The DC5225C® silicone surfactant is an excellent delivery system for emollients, moisturizers, sunscreen, anti-perspirant activities and pigments. The DC5225C® also provides stability to water molecules in silicone formulations and is important for clear water in oil emulsion synthesis technology.

According to one embodiment herein, the ethyl lactate is added in a quantity of 3.24% v/v for the synthesis of non-medicated liquid cleansing solution composition. Ethyl lactate is known as lactic acid or ethyl ester. Ethyl lactate is a monobasic ester formed from lactic acid and ethanol. Ethyl lactate is commonly used as a solvent. Ethyl lactate is considered biodegradable and is used as a water rinsable de-greaser in the cleansing solution composition.

According to one embodiment herein, the sesame oil is added in a quantity of 2.25% v/v for the synthesis of non-medicated liquid cleansing solution composition. The sesame oil moisturizes the skin. The sesame oil also removes toxins from surface of the skin. Sesame oil is high in anti-oxidants and has antibacterial properties.

According to one embodiment herein, Vitamin E is added in a quantity of 0.51% v/v for the synthesis of non-medicated liquid cleansing solution composition. Vitamin E is most powerful anti-oxidant. Vitamin E protects the skin from damage, repairs the skin tissue and moisturizes the skin tissue.

According to one embodiment herein, organic castile soap is added in a quantity of 0.29% v/v for the synthesis of non-medicated liquid cleansing solution composition. The castile soap cleans the rear area and private parts of an individual when wiped. Castile soap kills bacteria and germs.

According to one embodiment herein, sweet orange oil or fragrances are added in a quantity of 1.00% v/v for the synthesis of non-medicated liquid cleansing solution composition. Sweet orange oil or fragrances provide freshness and eliminates bad odor from the body parts. The sweet orange oil is a natural fragrance. The synthetic fragrances are added to replace sweet orange oil.

According to one embodiment herein, the Cyclomethicone, DC5225C® silicone surfactant, Ethyl lactate, Sesame oil, Vitamin E, Organic Castile soap, Sweet Orange oil and Fragrances are purchased or procured. The organic castile soap is treated before being introduced to the formulation. The water content in the organic castile soap is extracted. To extract the water content from organic castile soap, heat is applied until all of the water is evaporated. After heating the water content is evaporated and the organic castile soap in solid state remains. The solid organic castile soap is ready for use in the formulation.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a water-free, non-medicated liquid cleansing solution composition for personal hygiene and cleansing of private parts. The embodiments herein also provide a non-medicated liquid cleansing solution composition which is sprayed on tissue paper and is easily applied on the specific body area. Also the non-medicated liquid cleansing solution composition has no side effects. The non-medicated hygienic sanitary spray is used to moisten toilet paper/tissue paper. The non-medicated hygienic sanitary spray turns the toilet paper/tissue paper into a moist wipe. The moist wipe is used to clean the private body parts or any other body part.

According to one embodiment herein, a method of synthesizing a water-free, non-medicated liquid cleaning solution composition for personal care is provided. The method comprises the following steps. The cylomethicone, DC5225C®, ethyl lactate, sesame oil, Vitamin E, organic castile soap, sweet orange oil or a plurality of fragrances are purchased or procured. The organic castile soap is treated to extract a water content. The sesame oil, Vitamin E, ethyl lactate, DC5225C®, sweet orange oil or the plurality of fragrances and the treated organic castile soap are mixed to obtain a clear solution mixture. The clear solution mixture is added to the cyclomethicone. The clear solution mixture and cyclomethicone are mixed to attain a homogeneous mixture. The non-medicated liquid cleansing solution composition is synthesized for personal care and hygiene. The DC5225C® is a silicone surfactant.

According to one embodiment herein, the method of treating organic castile soap to remove water content involves drying the organic castile soap. The method of treating organic castile soap to remove water content comprises the following steps. The liquid organic castile soap is placed in a container. The container comprising liquid organic castile soap is heated. The water content from the organic castile soap is evaporated by applying a constant heat. The organic castile soap is obtained in a solid state.

According to one embodiment herein, the sesame oil is present in a preset quantity of 2.25% v/v. The Vitamin E is present in a preset quantity of 0.51% v/v. The ethyl lactate is present in a preset quantity of 3.24% v/v. The DC5225C® is present in a preset quantity of 3.50% v/v. The sweet orange oil or plurality of fragrances are present in a present quantity of 1.00% v/v. The dried organic castile soap is present in a preset quantity of 0.29% v/v. The cyclomethicone is preset in a preset quantity of 89.21% v/v.

According to one embodiment herein, the non-medicated liquid cleansing solution composition is sprayed or applied on tissue paper/toilet paper. The non-medicated liquid cleaning solution composition makes the tissue paper/toilet paper into a moist wipe. The moist wipe is used for cleaning a plurality of body parts. The moist wipe is specifically used for cleaning private body parts, groin, face, genital area and rear end.

According to one embodiment herein, the cyclomethicone is a volatile carrier. The cyclomethicone is compatible with the DC5225C®, silicone surfactant, ethyl lactate, sesame oil, Vitamin E, organic castile soap, sweet orange oil or the plurality of fragrances. The cyclomethicone is spread on the area of the application.

According to one embodiment herein, the DC5225C® is a delivery system for the non-medicated cleaning solution composition for personal care.

According to one embodiment herein, ethyl lactate is a solvent. The ethyl lactate is water rinsable grease or fat removal agent in the non-medicated liquid cleansing solution composition.

According to one embodiment herein, the sesame oil is a moisturizer in the non-medicated liquid cleansing solution composition. The sesame oil removes toxins from the surface of skin. The sesame oil is an anti-oxidant agent, and wherein the sesame oil is an anti-bacterial agent.

According to one embodiment herein, the organic castile soap kills bacteria and germs.

According to one embodiment herein, the sweet orange oil or plurality of fragrances are added in non-medicated liquid cleansing solution composition for personal care to eliminate bad odour from the body parts.

According to one embodiment herein, a water-free, non-medicated liquid cleaning solution composition for personal care, is provided. The composition comprises cyclomethicone, DC5225C®, ethyl lactate, sesame oil, Vitamin E, organic castile soap and sweet orange oil or plurality of fragrances. The DC5225C® is a silicon surfactant.

According to one embodiment herein, the sesame oil is present in a preset quantity of 2.25% v/v. The Vitamin E is present in a preset quantity of 0.51% v/v. The ethyl lactate is present in a preset quantity of 3.24% v/v. The DC5225C® is present in a preset quantity of 3.50% v/v. The sweet orange oil or plurality of fragrances are present in a present quantity of 1.00% v/v. The dried organic castile soap is present in a preset quantity of 0.29% v/v. The cyclomethicone is preset in a preset quantity of 89.21% v/v.

According to one embodiment herein, the cyclomethicone is a volatile carrier. The cyclomethicone is compatible with the DC5225C®, silicone surfactant, ethyl lactate, sesame oil, Vitamin E, organic castile soap, sweet orange oil or plurality of fragrances. The cyclomethicone is spread on the area of the application.

According to one embodiment herein, the DC5225C® is a delivery system for the non-medicated cleaning solution composition for personal care.

According to one embodiment herein, the ethyl lactate is a solvent. The ethyl lactate is water rinsable grease or fat removal agent in the non-medicated liquid cleansing solution composition.

According to one embodiment herein, the sesame oil is a moisturizer in the non-medicated liquid cleansing solution composition. The sesame oil removes toxins from the surface of skin. The sesame oil is an anti-oxidant agent and the sesame oil is an anti-bacterial agent.

According to one embodiment herein, the organic castile soap kills bacteria and germs.

According to one embodiment herein, the sweet orange oil or plurality of fragrances are added in non-medicated liquid cleansing solution composition for personal care to eliminate bad odour from the body parts.

According to one embodiment herein, the non-medicated liquid cleansing solution composition is sprayed or applied on tissue paper/toilet paper. The non-medicated liquid cleaning solution composition makes the tissue paper/toilet paper into a moist wipe. The moist wipe is used for cleaning plurality of body parts. The moist wipe is specifically used for cleaning private body parts, groin, face, genital area and rear end.

According to one embodiment herein, the non-medicated liquid cleansing solution composition that is intended to be sprayed on toilet paper/tissue paper. The non-medicated liquid cleansing solution composition is sprayed on toilet paper/tissue paper and applied on the specific body area (such as groin, or private body parts) where it gives smooth and soothing feel. The non-medicated liquid cleansing solution composition when sprayed on toilet paper/tissue paper gives similar qualities that of a baby wipe. The non-medicated liquid cleansing solution composition doesn't contain any harsh ingredients that could cause an allergic reaction in people.

According to one embodiment herein, the non-medicated liquid cleansing solution composition comprises of cyclomethicone, DC5225C® silicone surfactant, ethyl lactate, sesame oil, vitamin E, Castile soap, sweet orange oil and plurality of fragrances.

According to one embodiment herein, cyclomethicone is added in a quantity of 89.21% v/v for the synthesis of non-medicated liquid cleansing solution composition. The cyclomethicone is a volatile carrier, compatible with a wide range of cosmetic ingredients. The cyclomethicone has a low surface tension. The advantage of cyclomethicone in the composition is that, it imparts soft and silky skin after application; it spreads uniformly on the area of application and has a non-greasy nature.

According to one embodiment herein, DC5225C® is a silicone surfactant. The DC5225C® is added in a quantity of 3.50% v/v for the synthesis of non-medicated liquid cleansing solution composition. The DC5225C® silicone surfactant is an excellent delivery system for emollients, moisturizers, sunscreen, anti-perspirant activities and pigments. The DC5225C® also provides stability to water molecules in silicone formulations and is important for clear water in oil emulsion synthesis technology.

According to one embodiment herein, the ethyl lactate is added in a quantity of 3.24% v/v for the synthesis of non-medicated liquid cleansing solution composition. Ethyl lactate is known as lactic acid or ethyl ester. Ethyl lactate is a monobasic ester formed from lactic acid and ethanol. Ethyl lactate is commonly used as a solvent. Ethyl lactate is considered biodegradable and is used as a water rinsable de-greaser in the cleansing solution composition.

According to one embodiment herein, the sesame oil is added in a quantity of 2.25% v/v for the synthesis of non-medicated liquid cleansing solution composition. The sesame oil moisturizes the skin. The sesame oil also removes toxins from surface of the skin. Sesame oil is high in anti-oxidants and has antibacterial properties.

According to one embodiment herein, Vitamin E is added in a quantity of 0.51% v/v for the synthesis of non-medicated liquid cleansing solution composition. Vitamin E is most powerful anti-oxidant. Vitamin E protects the skin from damage, repairs the skin tissue and moisturizes the skin tissue.

According to one embodiment herein, organic castile soap is added in a quantity of 0.29% v/v for the synthesis of non-medicated liquid cleansing solution composition. Castile soap cleans the rear area and private parts of an individual when wiped. Castile soap kills bacteria and germs.

According to one embodiment herein, sweet orange oil or fragrances are added in a quantity of 1.00% v/v for the synthesis of non-medicated liquid cleansing solution composition. Sweet orange oil or fragrances provide freshness and eliminates bad odor from the body parts. The sweet orange oil is a natural fragrance. The synthetic fragrances are added to replace sweet orange oil.

According to one embodiment herein, the Cyclomethicone, DC5225C® silicone surfactant, Ethyl lactate, Sesame oil, Vitamin E, Organic Castile soap, Sweet Orange oil and Fragrances are purchased/procured. The organic castile soap is treated before being introduced to the formulation. The water content in the organic castile soap is extracted. To extract the water content from organic castile soap, heat is applied until all of the water is evaporated. After heating the water content is evaporated and the organic castile soap in solid state remains. The solid organic castile soap is ready for use in the formulation.

Figure 1:
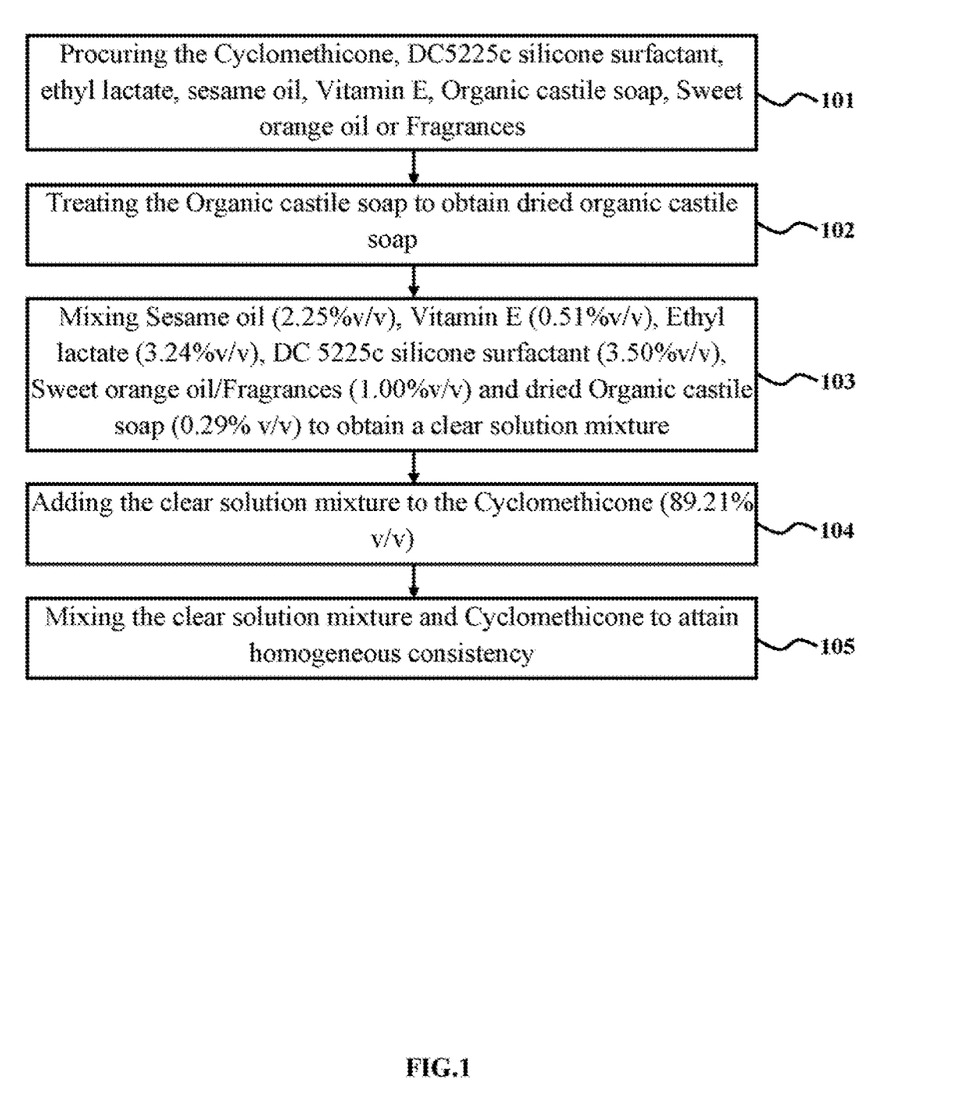
FIG. 1 illustrates a flow chart indicating a method for synthesizing a water-free, non-medicated hygienic sanitary spray for personal care and hygiene, according to one embodiment herein.

FIG. 1 illustrates a flow chart indicating a method for synthesizing non-medicated hygienic sanitary spray for personal care and hygiene, according to one embodiment herein. The cyclomethicone, DC5225C® silicone surfactant, Ethyl lactate, Sesame oil, Vitamin E, Organic castile soap, Sweet Orange oil or Fragrances are procured (101). The Organic castile soap is treated to obtain a dried organic castile soap (102). The Sesame oil (2.25% v/v), Vitamin E (0.51% v/v), Ethyl lactate (3.24% v/v), DC5225C® silicone surfactant (3.50% v/v), Sweet Orange oil/Fragrances (1.00% v/v) and the dried Organic Castile soap (0.29% v/v) are added to obtain a clear solution mixture (103). The clear solution mixture is added to the cyclomethicone (89.21% v/v) (104). The clear solution mixture and cyclomethicone are mixed to attain a homogeneous mixture and composition (105).

Figure 2:
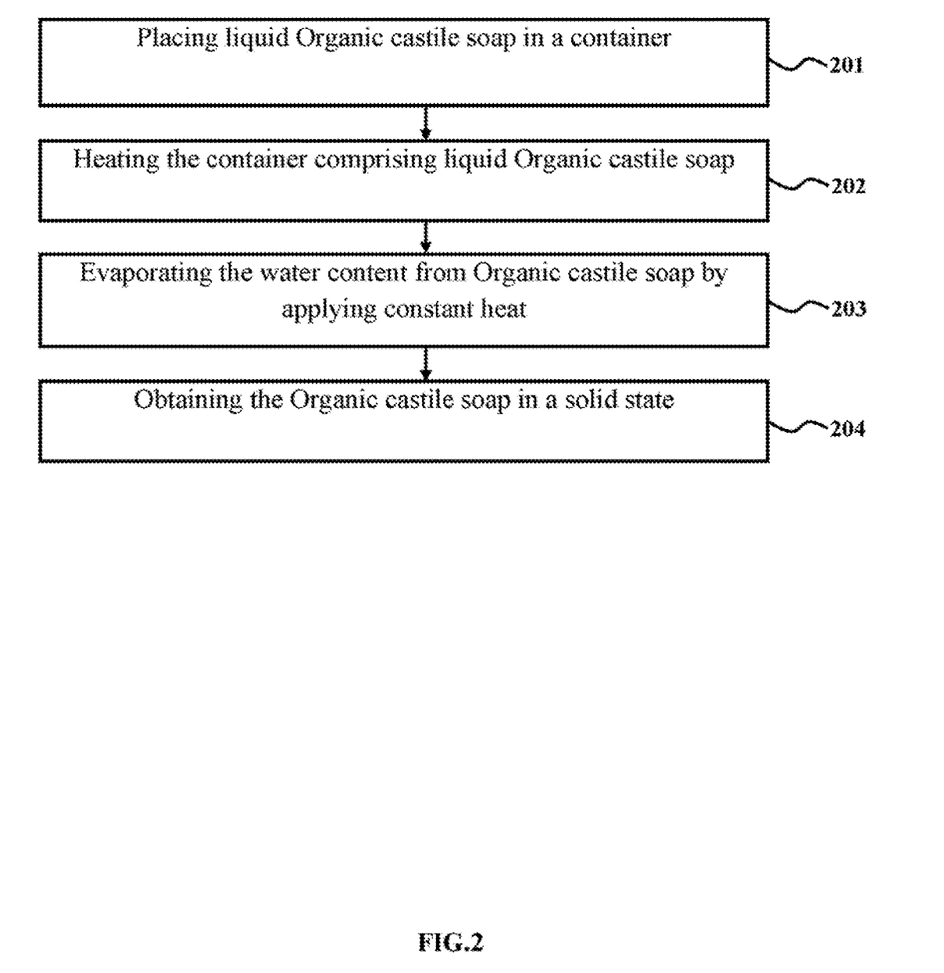
FIG. 2 illustrates a flow chart indicating a method for treating the liquid Organic castile soap, according to one embodiment herein.

FIG. 2 illustrates a flow chart indicating a method for treating the liquid Organic castile soap, according to one embodiment herein. The liquid organic castile soap in a container is placed in a container (201). The container comprising the liquid organic castile soap is heated (202). The water content from organic castile soap is evaporated by applying a constant heat (203). The organic castile soap is obtained in a solid state (204).

According to one embodiment herein, the non-medicated hygienic sanitary spray is used to moisten toilet paper. The non-medicated hygienic sanitary spray turns the toilet paper into a moist wipe. The water free non-medicated hygienic sanitary spray composition allows the composition to remain on top of the toilet paper/tissue paper instead of being absorbed by the toilet paper/tissue paper.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A method of synthesizing a water-free, non-medicated liquid cleaning solution composition for personal care, the method comprises the steps of:
   purchasing/procuring cylomethicone, DC5225C®, ethyl lactate, sesame oil, Vitamin E, organic castile soap, sweet orange oil or a plurality of fragrances;
   treating the organic castile soap to extract water content;
   mixing sesame oil, Vitamin E, ethyl lactate, DC5225C®, sweet orange oil or the plurality of fragrances and the treated organic castile soap to obtain a clear solution mixture;
   adding the clear solution mixture to the cyclomethicone; and
   mixing the clear solution mixture and cyclomethicone to attain a homogeneous mixture, and wherein the non-medicated liquid cleansing solution composition is synthesized for personal care and hygiene, and wherein the DC5225C® is a silicone surfactant.

2. The method according to claim 1, wherein the method of treating organic castile soap to remove water content involves drying the organic castile soap, and wherein the method of treating organic castile soap to remove water content comprises the steps of:
   placing the liquid organic castile soap in a container;
   heating the container comprising liquid organic castile soap;
   evaporating the water content from organic castile soap by applying constant heat; and
   obtaining the organic castile soap in a solid state.

3. The method according to claim 1, wherein the sesame oil is present in a preset quantity of 2.25% v/v, and wherein the Vitamin E is present in a preset quantity of 0.51% v/v, and wherein the ethyl lactate is present in a preset quantity of 3.24% v/v, and wherein the DC5225C® is present in a preset quantity of 3.50% v/v, and wherein the sweet orange oil or plurality of fragrances are present in a present quantity of 1.00% v/v, and wherein the dried organic castile soap is present in a preset quantity of 0.29% v/v, and wherein the cyclomethicone is preset in a preset quantity of 89.21% v/v.

4. The method according to claim 1, wherein the non-medicated liquid cleansing solution composition is sprayed or applied on tissue paper/toilet paper, and wherein the non-medicated liquid cleaning solution composition makes the tissue paper/toilet paper into a moist wipe, and wherein the moist wipe is used for cleaning plurality of body parts, and wherein the moist wipe is specifically used for cleaning private body parts, groin, face, genital area and rear end.

5. The method according to claim 1, wherein the cyclomethicone is a volatile carrier, and wherein the cyclomethicone is compatible with the DC5225C®, silicone surfactant, ethyl lactate, sesame oil, Vitamin E, organic castile soap, sweet orange oil or the plurality of fragrances, and wherein the cyclomethicone is spread on the area of the application.

6. The method according to claim 1, wherein the DC5225C® is a delivery system for the non-medicated cleaning solution composition for personal care.

7. The method according to claim 1, wherein ethyl lactate is a solvent, and wherein the ethyl lactate is water rinsable grease or fat removal agent in the non-medicated liquid cleansing solution composition.

8. The method according to claim 1, wherein the sesame oil is a moisturizer in the non-medicated liquid cleansing solution composition, and wherein the sesame oil removes toxins from the surface of skin, and wherein the sesame oil is an anti-oxidant agent, and wherein the sesame oil is an anti-bacterial agent.

9. The method according to claim 1, wherein the organic castile soap kills bacteria and germs.

10. The method according to claim 1, wherein the sweet orange oil or plurality of fragrances are added in non-medicated liquid cleansing solution composition for personal care to eliminate bad odour from the body parts.

11. A water-free, non-medicated liquid cleaning solution composition for personal care, the composition comprises of:
   a cyclomethicone;
   a DC5225C®;
   an ethyl lactate;
   a sesame oil;
   a Vitamin E;
   an organic castile soap; and a sweet orange oil or plurality of fragrances, and wherein DC5225C® is a silicon surfactant.

12. The composition according to claim 11, wherein the sesame oil is present in a preset quantity of 2.25% v/v, and wherein the Vitamin E is present in a preset quantity of 0.51% v/v, and wherein the ethyl lactate is present in a preset quantity of 3.24% v/v, and wherein the DC5225C® is present in a preset quantity of 3.50% v/v, and wherein the sweet orange oil or plurality of fragrances are present in a present quantity of 1.00% v/v, and wherein the dried organic castile soap is present in a preset quantity of 0.29% v/v, and wherein the cyclomethicone is preset in a preset quantity of 89.21% v/v.

13. The composition according to claim 11, wherein the cyclomethicone is a volatile carrier, and wherein the cyclomethicone is compatible with the DC5225C®, silicone surfactant, ethyl lactate, sesame oil, Vitamin E, organic castile soap, sweet orange oil or plurality of fragrances, and wherein the cyclomethicone is spread on the area of the application.

14. The composition according to claim 11, wherein the DC5225C® is a delivery system for the non-medicated cleaning solution composition for personal care.

15. The composition according to claim 11, wherein ethyl lactate is a solvent, and wherein the ethyl lactate is water rinsable grease or fat removal agent in the non-medicated liquid cleansing solution composition.

16. The composition according to claim 11, wherein the sesame oil is a moisturizer in the non-medicated liquid cleansing solution composition, and wherein the sesame oil removes toxins from the surface of skin, and wherein the sesame oil is an anti-oxidant agent, and wherein the sesame oil is an anti-bacterial agent.

17. The composition according to claim 11, wherein the organic castile soap kills bacteria and germs.

18. The composition according to claim 11, wherein the sweet orange oil or plurality of fragrances are added in non-medicated liquid cleansing solution composition for personal care to eliminate bad odour from the body parts.

19. The composition according to claim 11, wherein the non-medicated liquid cleansing solution composition is sprayed or applied on tissue paper/toilet paper, and wherein the non-medicated liquid cleaning solution composition makes the tissue paper/toilet paper into a moist wipe, and wherein moist wipe is used for cleaning plurality of body parts, and wherein the moist wipe is specifically used for cleaning private body parts, groin, face, genital area and rear end.

* * * * *